United States Patent [19]

Breipohl et al.

[11] Patent Number: 5,166,394

[45] Date of Patent: Nov. 24, 1992

[54] COUPLING REAGENT FOR PEPTIDE SYNTHESIS

[75] Inventors: Gerhard Breipohl, Frankfurt am Main; Wolfgang König, Hofheim am Taunus, both of Fed. Rep. of Germany

[73] Assignee: Hoechst Aktiengesellschaft, Frankfurt am Main, Fed. Rep. of Germany

[21] Appl. No.: 703,854

[22] Filed: May 21, 1991

[30] Foreign Application Priority Data

May 23, 1990 [DE] Fed. Rep. of Germany ....... 4016596

[51] Int. Cl.$^5$ ................... C07C 255/15; C07C 253/30
[52] U.S. Cl. ...................... 558/301; 558/384
[58] Field of Search ................... 558/301, 384

[56] References Cited

U.S. PATENT DOCUMENTS

| | | | |
|---|---|---|---|
| 2,738,363 | 3/1956 | Godefroi | 558/301 X |
| 3,296,274 | 1/1967 | Stafiej et al. | 558/384 X |
| 4,341,707 | 7/1982 | Ogura et al. | 558/301 X |
| 4,478,848 | 10/1984 | Brandes et al. | 558/301 X |

FOREIGN PATENT DOCUMENTS 0646143  11/1984  Switzerland .................. 558/301

OTHER PUBLICATIONS

Kogler, et al., Tetrahedron Letters, vol. 30, No. 15, pp. 1931–1934, (1989).
Mohamed, et al., Tetrahedron Letters, vol. 30, No. 15, pp. 1935–1938, (1989).
Loubinoux, et al., Tetrahedron Letters, vol. 30, No. 15, pp. 1939–1942 (1989).
Konig et al., "Perchloric Acid in Peptide Chemistry" Peptides 1990; pp. 143–145 (1991).
Dourtoglou et al., Synthesis, pp. 572–574 (1984).
Itoh, Chemistry and Biology of Peptides, pp. 365–367 (1972).
Knorr et al., Tetrahedon Letters, vol. 30, No. 15, (1989) pp. 1927–1930.

*Primary Examiner*—Joseph P. Brust
*Attorney, Agent, or Firm*—Finnegan, Henderson, Farabow, Garrett and Dunner

[57] ABSTRACT

Novel compounds of the formula I

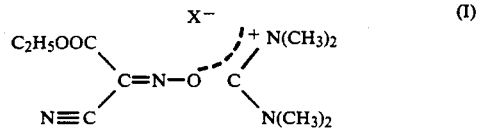

in which X is an anion, and a process for the preparation thereof, are described. Compounds of the formula I are used as coupling reagents in peptide synthesis.

4 Claims, No Drawings

COUPLING REAGENT FOR PEPTIDE SYNTHESIS

DESCRIPTION

The invention relates to a coupling reagent for peptide synthesis.

Synthesis, 1984, 572-574 and Tetrahedron Letters, Vol. 30, No. 15 (1989, 1927-1939 disclose uronium salts such as 2-(1H-bcnzotriazol-1-yl)-1,1,3,3-tetramethyluronium hexafluorophosphate (HBTU), 2-(1H-benzotriazol-1-yl)-1,1,3,3-tetramethyluronium hexafluoroborate (TBTU), 2-(3,4-dihydro-4-oxo-1,2,3-benzotriazin-3-yl)-1,1,3,3-tetramethyluronium tetrafluoroborate (TDBTU), 2-(2-oxo-1 [2H]-pyridyl)-1,1,3,3-tetramethyluronium tetrafluoroborate (TPTU), 2-succinimido-1,1,3,3-tetramethyluronium tetrafluoroborate (TSTU), 2-(5-norbornene-2,3-dicarboximido)-1,1,3,3-tetramethyluronium tetrafluoroborate (TNTU). Ethyl 2-hydroxyimino-2-cyanoacetate and its use as additive for suppressing racemization in peptide couplings has also been disclosed (Masumi Itoh, Peptides: Chemistry and Biology of Peptides, Proceedings of 5 the fourth American Peptide Symposium, pages 365-367, Ed.: R. Walter, J. Meienhofer, Ann Arbor Science Publishers 1972).

Since the use of dichloromethane and acetonitrile which are hazardous to health and toxic is indispensable in the preparation of known uronium salts such as TBTU, the object of the invention is to find novel coupling reagents for peptide synthesis which are distinguished, inter alia, by a straightforward preparation process.

This object is achieved according to the invention by the compound of the formula I

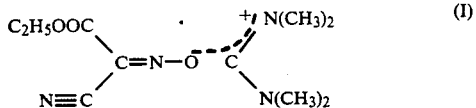

in which X is an anion.

Particularly preferred compounds of the formula I are those in which X is $BF_4^-$ or $PF_6^-$. Particular mention may be made of O-[(cyano(ethoxycarbonyl methylidene)amino]-1,1,3,3-tetramethyluronium tetrafluoroborate (TOTU).

The compounds according to the invention are distinguished by a high activation potential, straightforward preparation (one-pot reaction) and high solubility. The only solvents used in the preparation are toluene and acetone. In addition, the sodium salt of the oxime employed in the reaction can be obtained directly from ethyl cyanoacetate. The by-products resulting from the activation of a carboxyl group with compounds of the formula I are tetramethylurea and ethyl 2-hydroxyimino-2-cyanoacetate, which can readily be extracted in the water. Moreover, the anion of the oxime is yellow in color and can therefore be readily detected on extraction of the reaction mixture with, for example, bicarbonate. Furthermore, the use of the coupling reagents of the formula I is possible both in classical peptide synthesis and in solid-phase peptide synthesis. Various reagents can be used as additive to suppress racemization, such as, for example, 1-hydroxybenzotriazole (HOBt), 3-hydroxy-4-oxo-3,4-dihydro-1,2,3-benzotriazine (HOObt), 2-hydroxypyridine N-oxide, ethyl 2-hydroxy-2-cyanoacetate and the like.

The invention furthermore relates to a process for preparing compounds of the formula I, which comprises reacting tetramethylurea with oxalyl chloride or phosgene in toluene, mixing the resulting intermediate of the formula II, after dilution of the solution with acetone, successively with the sodium salt of the desired anion and with the sodium salt of ethyl 2-hydroxyimino-2-cyano-acetate (M. Conrad, A. Schulze, Chem. Ber. 42 1909) 735), filtering off the precipitate with suction and washing it with acetone, and crystallizing the product after addition of isopropanol to the filtrate.

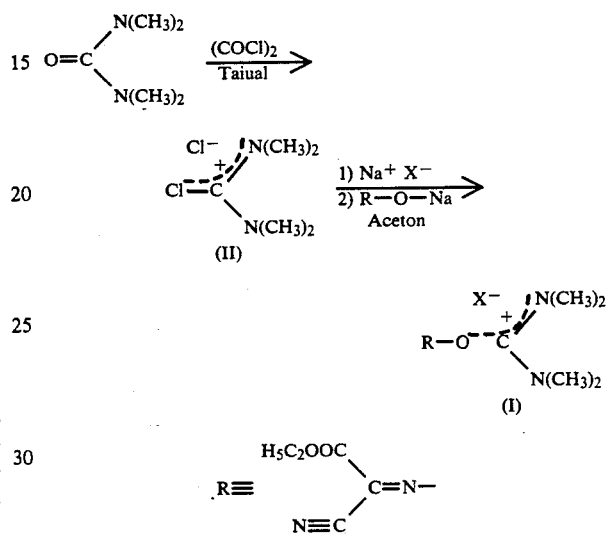

Coupling reactions with compounds of the formula I are normally carried out in suitable polar aprotic solvents such as, for example, dimethylformamide (DMF), N-methylpyrrolidone (NMP) or acetonitrile. When an excess of compound of the formula I is used, it is also possible to employ mixed aqueous systems.

One to three equivalents of a tertiary organic base are added in the activation of a carboxylic acid or of a specific N-protected amino acid.

When the coupling reagent according to the invention is used in solid-phase peptide synthesis, the activation of the amino acid preferably takes place separately. When an automatic peptide synthesizer, for example ABI 430 A (from Applied Biosystems, USA) is used, the coupling reagent is introduced in a defined amount into the cartridges either with the amino acid as solid substance or as solution. Activation is carried out by addition of a base (1-2 equivalents). Where appropriate, an additive suppressing racemization as described above is included. The preactivation time is 3-30 minutes.

The peptide coupling is carried out by known methods, as described, for example, in EP-A 271 865 (HOE 86/F 308).

The preparation of the compounds of the formula I, and some examples of their use in synthesis are given hereinafter.

1.

O-[Cyano(ethoxycarbonyl)methylidene)amino]-1,1,3,3-tetramethyluronium tetrafluoroborate (TOTU)

121 ml (1 mole) of tetramethylurea are dissolved in 300 ml of toluene. Then, while stirring vigorously and under a protective gas (weak stream of $N_2$), 86.4 ml (1 mole) of oxalyl chloride dissolved in 100 ml of toluene are added dropwise in 20 minutes. The mixture is stirred at 50°-55° C. until no more CO$_2$ escapes. The resulting suspension of the intermediate which has formed is then allowed to cool to room temperature, and 600 ml of dry acetone and then 104.3 g (0.95 mole) of sodium tetrafluoroborate (finely powdered) are added. The suspension is stirred at room temperature for 1 h and 156.9 g (0.95 mole) of the sodium salt of ethyl hydroxyiminocyanoacetate are added in portions. The mixture is cooled overnight and then the precipitate (sodium chloride and product) is filtered off. The filtrate is concentrated to about 500 ml in a rotary evaporator and then 1.2 l of dry isopropanol are added and the mixture is stirred at 40° C. for 30 minutes. The precipitated product is filtered off with suction and washed with a little isopropanol (about 100 ml) and dried in a desiccator. N$_1$:57.3 g The product/NaCl mixture is stirred with 400 ml of dry acetone at 40° C. for 20 minutes and filtered hot. The filtrate is concentrated to about 100 ml and 300 ml of dry isopropanol are added, the mixture is stirred at 40° C. for 20 minutes and the product is filtered off with suction, washed with isopropanol and dried. N$_2$:43.6 g.

This procedure is carried out twice more with the NaCl/product
mixture N$_3$:31.5 g, N: 5.3 g.
Total yield:N$_1$-N$_4$:137.6 g (44.1%).
Melting point 142°-145° C. with decomposition

| Elemental analysis: | C | H | N | Cl |
| --- | --- | --- | --- | --- |
| calculated: | 36.58 | 5.22 | 17.18 | 0% |
| found: | 36.8 | 5.2 | 17.1 | <0.3% |

A) Sodium salt of ethyl hydroxyiminocyanoacetate a) 1 mole of ethyl hydroxyiminocyanoacetate is dissolved in 400 ml of methanol (or ethanol) and, while cooling, a solution of 1 mole of NaOH in 300 ml of methanol is added dropwise. The mixture is then evaporated to dryness and twice mixed with 200 ml of toluene and evaporated to dryness. The resulting sodium salt is again dried in a desiccator under high vacuum and then finely powdered.

b) Directly from ethyl cyanoacetate

Nitrosation of ethyl cyanoacetate with sodium nitrite and acetic acid [M. Conrad, A. Schulze, Chem. Ber. 42, 735 (1909)] results in the sodium salt directly. The latter is extensively dried and several times suspended in hot ethyl acetate and toluene and evaporated to dryness in order to remove acetic acid and water. Crystallization from ethyl acetate where appropriate. The product ought to contain no sodium acetate (NMR check).

2. Fmoc-D-Hyp-Gly-OtBu 1.4 g of Fmoc-D-Hyp-OH are dissolved in 25 ml of dry acetonitrile and then 1.05 g of H-Gly-OtBu and 0.445 g of N-hydroxypyridone are added. Then 1.31 g of O-[(cyano(ethoxycarbonyl)methylidene)amino]-1,1,3,3-tetramethyluronium tetrafluoroborate (TOTU) are introduced in/portions within 10 minutes, as well as 1.03 ml of diisopropylethylamine in 15 ml of DMF dropwise over the course of 15 minutes. After 1 h, the mixture is concentrated, the residue is taken up in ethyl acetate and extraction with sodium chloride solution is carried out. The organic phase is dried over sodium sulfate and evaporated to dryness. The remaining oil is taken up in a little ether and added dropwise to petroleum ether while stirring. The flocculent precipitate is filtered off with suction and dried in vacuo.
Yield:671 mg.
MS (FAB):467 (M+H).

3. Fmoc-Leu-Arg-Pro-Azagly amide

To a solution of 136.5 mg of H-Pro-Azagly amide HClO$_4$ in 5 ml of DMF are added 255 mg of Fmoc-Leu-Arg-OH and, at 0° C. with stirring, 164 mg of O-[(cyano(ethoxycarbonyl)methylidene)amino]-1,1,3,3-tetramethyluronium tetrafluoroborate (TOTU) and 0.065 ml of N-ethylmorpholine. The mixture is then stirred at 0° C. for 1 h and at room temperature overnight. Insolubles are then filtered off, and the filtrate is concentrated. The residue is dissolved in 10 ml of pentanol and extracted three times with 10 ml of saturated aqueous bicarbonate solution. The organic phase is concentrated, triturated with diethyl ether and dried.
Yield:260 mg.
MS (FAB):664 (M+H).

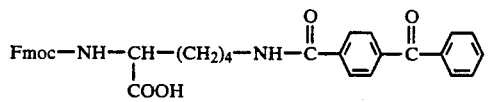

2.22 g of 2-hydroxypyridine N-oxide and 6.56 g of TOTU are added to a solution of 4.52 g of benzophenone-4-carboxylic acid in 200 ml of DMF and then, while stirring, 5.23 ml of diisopropylethylamine are added dropwise. The mixture is left to react at room temperature for 30 minutes and then 8 1 g of Fmoc—Lys—OH .HCl are added. The mixture is subsequently allowed to react at room temperature for 3 h and then evaporated to dryness in vacuo. The residue is taken up in 200 ml of ethyl acetate and washed three times with 20 ml each of KHSO$_4$/K$_2$SO$_4$ solution and H$_2$O. The organic phase is dried over Na$_2$SO$_4$ and evaporated to dryness. The residue is taken up in 50 ml of isopropanol and the solution is stirred into 500 ml of diisopropyl ether, and the precipitated product is filtered off with suction and washed with diisopropyl ether. 4.76 g of the final compound are obtained after drying under high vaccum.
MS (FAB):577 (M+H).

5. Synthesis of Ac-D-Nal-pCl-D-Phe-D-Trp-Ser(tBu)-Tyr(tBu)-OtBu and racemization test To a solution of 64.3 mg (0.25 mmol) Ac—D—Nal—OH and 244.3 mg of H-pCl-D-Phe-D-Trp-Ser(tBu)-Tyr(tBu)-OtBu. Tos—OH in 5 ml of DMF, 0.25 mmol coupling reagent were added at 0 ° C. After stirring for 1 h at 0° C. and over night at room temperature the mixture was filtered and the filtrate concentrated in vacuo. The residue was treated with concentrated bicarbonate solution. The unsoluble product was filtered, washed with water, treated with a potassium sulfate/potassium-hydrogensulfate solution, filtered, washed with water and dried in vacuo.

Racemization of the coupled Ac—D—Nal—OH was determined by HPLC using a Nucelosil 120-5 C8 250/8/4 column and methanol/water 7/3 as solvent with a flow of 1 ml/min. Detection wavelength was 215 nm. The title compound eluted at a retention time of 37.7 min the reacemized product at 49.1 min.

The following table shows the coupling procedures used and the result of the racemization test

| coupling procedure | % L-Nal |
|---|---|
| DCC/HOObt/NEM | 1.21 |
| TOTU/HOObt/2 equ. NEM | 0.63 |

6. Solid phase synthesis of H-D-Arg-Arg-Pro-Hyp-Gly-Thi-Ser-D-Tic-Oic-Arg—OH The synthesis was performed with an automated peptide synthesizer Applied Biosystems model 430A using Fmoc amino acids and programs modified by us. The peptide was synthesized on 1 g of Fmoc-Arg(Mtr)-Wang resin (loading 0.4 mmol/g) according to the following stepwise procedure
1) removal of Fmoc protecting group with piperidine/DMF
2) washing of resin with DMF
3) coupling of the amino acid activated with TOTU*
4) washing of the resin with DMF These procedure was repeated for each amino acid until the peptide chain was assembled

*) Preactivation of the amino acids was performed in the cartridge according to the following procedure 1 mmol of Fmoc amino acid were weighed into the cartridge and 2 ml of a 0.5 molar solution of TOTU in DMF, 2 ml of DMF-solution (0.5 molar of N-hydroxypyridone and 1 molar of diisopropylethylamine) and 4 ml of DMF were added. The mixture was mixed for 1 min and then transferred to the reaction vessel. Coupling time was 20 to 30 min. The amino acid derivatives used were the following: Fmoc-Oic—OH, Fmoc-D-Tic—OH, Fmoc-Ser(tBu)—OH, Fmoc-Thi—OH, Fmoc-Gly—OH, Fmoc-Hyp—OH, Fmoc-Pro—OH, Fmoc-Arg(Mtr)—OH, Fmoc-D-Arg(Mtr)—OH.

After the synthesis was finished the remaining Fmoc group was removed by treatment with piperidine in DMF. Then the resin was washed with DMF, dichloromethane, isopropanol and methyl-tert.butyl-ether and then dried in vacuo.

Yield:1.42 g of peptide resin. The peptide was cleaved off from the resin by treatment with 0.9 ml m-cresole in 1.42 ml dichloromethane followed by addition of 14 ml trifluoroacetic acid and 1 ml trimethylsilylbromide. After 2.5 h the mixture was filtered into 200 ml cold methyl-tert.butylether. The precipitated solid was filtered off, then dissolved in water and the aqueous solution extracted with ethylacetate to remove scavengers. The aqueous solution was then treated with ion exchange resin ®Dowex IRA 93 (acetate form), filtered and lyophilized. The crude peptide (267 mg) was purified further by chromatography on a ®Sephadex LH 20 column with 10% acetic acid as eluent.

7. Synthesis of [Boc—Phe—Val—NH—CH(CH$_2$—C$_6$H$_5$)—CH(OH)-]$_2$—

828 mg [H—Val—NH—CH(CH$_2$—C$_6$H$_5$)—CH(OH)—]$_2$. 2 HCl were dissolved in 40 ml DMF. Then 995 mg Boc-Phe-OH were added followed by 533 mg ethyl-2-hydroxyimino-2-cyanoacetate and at 0° C. 1.23 g TOTU. Then 4.1 ml diisopropylethylamino were added dropwise and stirred for 1 h. The solvent was removed in vacuo and the residue partitioned between dichloromethane and water. The organic layer was washed with KHSO$_4$/K$_2$SO$_4$ solution, saturated bicarbonate solution and water. After drying over Na$_2$SO$_4$ the organic layer was evaporated to dryness. The residue was dissolved in warm ethylacetate and precipitated with ether. The solid was filtered off, washed with ether and dried in vacuo.

Yield:896 mg.

| Abbreviations used: | |
|---|---|
| Ac | Acetyl |
| Arg | Arginine |
| Azagly | Azaglycine |
| Boc | tert. Butoxycarbonyl |
| DCC | Dicyclohexylcarbodiimid |
| DMF | Dimethylformamide |
| Fmoc | 9-Fluorenylmethoxycarbonyl |
| Gly | Glycine |
| HOBt | 1-Hydroxybenzotriazol |
| HOObt | 3-Hydroxy-4-oxo-3,4-dihydro-1,2,3-benzotriazin |
| D-Hyp | D-Hydroxyproline |
| Leu | Leucine |
| Mtr | 2,3,5-Trimethyl-4-methoxyphenylsulfonyl |
| D-Nal | D-2-Naphthylalanin |
| NEM | N-Ethylmorpholin |
| Oic | cis,endo Octahydroindole |
| OtBu | O-tert.Butyl |
| D-Phe | Phenylalanine |
| Pro | Proline |
| Ser | Serine |
| Thi | 2-Thienylalanin |
| D-Tic | 1,2,3,4-Tetrahydroisochinolin-3-yl-carbonyl |
| Tos | Toluol-4-sulfonyl |
| D-Trp | D-Tryptophan |
| Tyr | Tyrosine |
| Val | Valine |

We claim:
1. A compound of the formula I

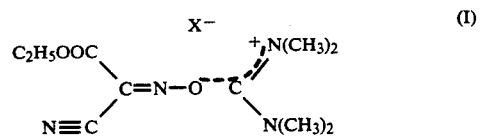

in which X is BF$_4^-$ or PF$_6^-$.

2. A compound of the formula I as claimed in claim 1, wherein X is BF$_4^-$.

3. A process for preparing a compound of the formula I as claimed in claim 1, which comprises reacting tetramethylurea with oxalyl chloride or phosgene in toluene, mixing the resulting product of the formula II,

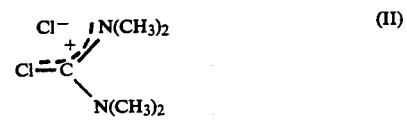

after dilution of the solution with acetone, successively with the sodium salt of the desired anion and with the sodium salt of ethyl 2-hydroxyimino-2-cyanoacetate, filtering off the precipitate with suction and washing it with acetone, and crystallizing the product after addition of isopropanol to the filtrate.

4. A process for preparing a compound of the formula I as claimed in claim 1, which comprises the steps of (a) reacting tetramethylurea with oxalyl chloride or phosgene in toluene, stirring the mixture at 50°–55° C. (b) mixing the resulting product of the formula II,

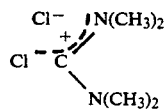 (II)

after cooling to room temperature and dilution of the solution with acetone, successively with the sodium salt of $BF_4^-$ or $PF_6^-$ and with the sodium salt of ethyl 2-hydroxyimino-2-cyanoacetate, (c) filtering off the precipitate of step (b) with suction and washing said precipitate with acetone, and (d) crystallizing the product of step (c) after addition of isopropanol to said precipitate.

* * * * *

UNITED STATES PATENT AND TRADEMARK OFFICE
CERTIFICATE OF CORRECTION

PATENT NO. : 5,166,394
DATED : November 24, 1992
INVENTOR(S) : Gerhard Breipohl et al.

It is certified that error appears in the above-indentified patent and that said Letters Patent is hereby corrected as shown below:

On title page, item [54] and col. 1, line 1, title of invention should read
--URONIUM COUPLING REAGENT FOR PEPTIDE SYNTHESIS--

Abstract, Title Page, change (Formula 1)

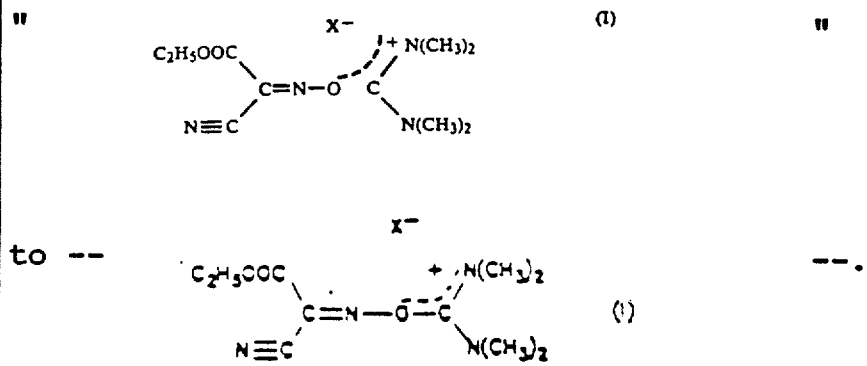

Claim 1, column 6, change (in Formula 1) change "O C"
to --O-C--.

UNITED STATES PATENT AND TRADEMARK OFFICE
CERTIFICATE OF CORRECTION

PATENT NO. : 5,166,394
DATED : November 24, 1992
INVENTOR(S) : Gerhard Breipohl et al.

It is certified that error appears in the above-indentified patent and that said Letters Patent is hereby corrected as shown below:

Claim 1, column 6, line 46, change "$BF_4$ -or $PF_6$-" to --$BF_4^-$ or $PF_6^-$--.

Claim 2, column 6, line 48, change "$BF_4$-" to --$BF_4^-$--.

Claim 4, column 7, line 1, change "50°-55°C.," to --50-55°C,--; (In Formula II)

change "
$$Cl-C\begin{matrix}Cl^- \\ + \end{matrix}\begin{matrix}N(CH_3)_2 \\ N(CH_3)_2\end{matrix} \quad (II)$$
"

to --
$$Cl=C\begin{matrix}Cl^- \\ + \end{matrix}\begin{matrix}N(CH_3)_2 \\ N(CH_3)_2\end{matrix} \quad (II)$$
--.

UNITED STATES PATENT AND TRADEMARK OFFICE
CERTIFICATE OF CORRECTION

PATENT NO. : 5,166,394
DATED : November 24, 1992
INVENTOR(S) : Gerhard Breiphol et al It is certified that error appears in the above-indentified patent and that said Letters Patent is hereby corrected as shown below:

Claim 4, column 8, line 3, change "$BF_4-$ or $PF_6$ to --$BF_4^-$ or $PF_6^-$--.

Signed and Sealed this

First Day of March, 1994

*Attest:*

BRUCE LEHMAN

*Attesting Officer*   *Commissioner of Patents and Trademarks*